(12) United States Patent
Schindler et al.

(10) Patent No.: US 7,393,138 B2
(45) Date of Patent: Jul. 1, 2008

(54) INTEGRATED COOLANT CONDUCTION FOR A COMPUTER TOMOGRAPH

(75) Inventors: Edgar Schindler, Speichersdorf (DE); Georg Walberer, Kastl (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/580,150

(22) PCT Filed: Nov. 11, 2004

(86) PCT No.: PCT/EP2004/052928

§ 371 (c)(1),
(2), (4) Date: Mar. 16, 2007

(87) PCT Pub. No.: WO2005/048843

PCT Pub. Date: Jun. 2, 2005

(65) Prior Publication Data

US 2007/0274437 A1   Nov. 29, 2007

(30) Foreign Application Priority Data

Nov. 20, 2003   (DE) ............................. 103 54 225

(51) Int. Cl.
*H01J 35/10* (2006.01)
(52) U.S. Cl. .................... 378/199; 378/15; 378/193
(58) Field of Classification Search ............ 378/4–20, 378/193–200
See application file for complete search history.

(56) References Cited

U.S. PATENT DOCUMENTS

| 4,866,743 | A | 9/1989 | Kroener ..................... 378/4 |
| 5,448,608 | A | 9/1995 | Swain et al. ................ 378/4 |
| 6,412,979 | B1 | 7/2002 | Hell et al. ................. 378/200 |
| 2007/0053500 | A1* | 3/2007 | Distler et al. .............. 378/199 |

FOREIGN PATENT DOCUMENTS

| DE | 421 78 74 A1 | 12/1993 |
| DE | 295 10 802 | 9/1995 |
| EP | 0 292 690 A1 | 4/1988 |

OTHER PUBLICATIONS

International Search Report.
International Preliminary Examination Report with English Translation.
DE—Office Action dated Jul. 19, 2004 with an English translation.

* cited by examiner

*Primary Examiner*—Courtney Thomas
(74) *Attorney, Agent, or Firm*—Brinks Hofer Gilson & Lione

(57) ABSTRACT

A support cradle for a computer tomorgraph, in which the rotating body together with the X-ray emitter and the X-ray detector, which is situated opposite said emitter, can be ratably mounted. The support cradle includes a suitable pedestal that has two vertical supports, in addition to a gantry, which is mounted between the vertical supports and can be rotated about a horizontal transverse axis. According to the invention, the support cradle comprises a cooling device that is simple to manufacture. Said device is configured at least partially as a hollow section. A cavity in the support cradle acts as a conduit for supplying or evacuating a coolant.

14 Claims, 2 Drawing Sheets

INTEGRATED COOLANT CONDUCTION FOR A COMPUTER TOMOGRAPH

BACKGROUND

A support cradle or stand is provided for a computed tomography system. A computed tomography system has such a support cradle or stand. A computed tomography system is an apparatus for generating a three-dimensional image of an object being examined, in particular a patient, using radiological diagnostic methods.

A conventional computed tomography system, of the kind known for instance from European Patent Disclosure EP 0 292 690 A1, includes a rotating body with a central opening, into which the object being examined is positioned. The rotating body includes an X-ray emitter for passing X-radiation through the object being examined, and an X-ray detector, diametrically opposite the X-ray emitter, for making an X-ray image. The rotating body is supported rotatably on a support cradle. By rotating the rotating body, the object being examined can be exposed to radiation from many directions. From the information in the X-ray images, a three-dimensional image of the object being examined is created using electronic data processing.

The dissipation of the heat that occurs in the X-ray emitter and the X-ray detector may be difficult. Local air cooling, for instance by a fan, may be used only to a limited extent if at all in a computed tomography system. The draft necessarily created is unwanted for health reasons. Supplying and evacuating a gaseous or liquid coolant using rigid or flexible coolant lines may be complicated and expensive, especially since such lines must not hinder the required rotatability of the rotating body.

For this reason, a computed tomography system is often equipped with a complex cooling system. For instance, from the aforementioned EP 0 292 690 A1, a computed tomography system is known. A first cooling loop cools the X-ray emitter. The first cooling loop exchanges the absorbed heat with a second cooling loop, which is placed partly in an annular chamber formed between the rotating body and the support cradle. Cooling air flows through the annular chamber, and this cooling air is itself cooled by means of a third cooling loop, which is water-driven.

From German Patent Disclosure DE 42 17 874 A1, a mobile radiological diagnostic system is also known. An X-ray emitter and an X-ray detector are secured, diametrically opposite one another, on a support cradle that includes a C-arch. For cooling the X-ray emitter, a double hose is provided, which extends partly inside the support cradle.

SUMMARY

A support cradle for a computed tomography system may have more easily implemented cooling conduction. A computed tomography system may have a suitable and easily implemented cooling device.

A support cradle for the rotating body of a computed tomography system is embodied at least partly as a hollow section. The hollow chamber embodied in the support cradle is used as a conduit for supplying or evacuating a coolant.

By integrating at least part of the conduit system of the cooling device with the support cradle for a computed tomography system, a compact and advantageous layout of the lines is attained. In particular, because the coolant is carried in the interior of the support cradle, a freely suspended line is avoided, improving the manipulation of the computed tomography system and reducing the vulnerability of the cooling device to malfunction. Integrating the coolant layout with the support cradle is moreover structurally simple and is uncomplicated and inexpensive to attain. A support cradle embodied at least partly as a hollow section is advantageous in view of its comparatively low weight with high stability.

The support cradle may be embodied such that in the support cradle interior, two hollow chambers extend essentially parallel and are fluidically separated from one another. A first of these hollow chambers is used as a conduit for supplying the coolant, where the second hollow chamber is used as a conduit for evacuating the coolant.

The support cradle expediently includes a pedestal with two vertical supports. In addition, the support cradle expediently includes a supporting ring, which is rotatably supported between the vertical supports about a horizontal transverse axis. The supporting ring of the construction, which because the supporting ring is suspended on both sides is also known as a "gantry," in turn serves to support a rotating body or carriage.

The pedestal of the support cradle expediently includes a base plate, embodied as a hollow section, in which at least one but preferably two transversely extending hollow chambers are fluidically separated from one another. The hollow chambers are used as transverse conduits for the coolant. Via these transverse conduits, a blower and cooling unit can be especially expediently connected. The blower and cooling unit is preferably disposed on the base plate to save space.

Alternatively or in addition, the supporting ring of the support cradle is embodied as a hollow section. In the interior of the supporting ring, at least one but preferably two annular hollow chambers, separated from one another, are embodied as an annular conduits for the coolant. In a stable and structurally simple geometrical configuration, the supporting ring has a substantially L-shaped profile, and one annular conduit is disposed in each arm of the L-shaped section.

Supplying or evacuating the coolant from an annular conduit of the supporting ring is expediently done via the transverse axis about which the supporting ring is rotatably supported. The supply and evacuation of the coolant are independent of the rotary position of the supporting ring. For the sake of the coolant layout, a shaft segment secured to the circumference of the supporting ring is a hollow form and communicates with the corresponding annular conduit of the supporting ring.

Each annular conduit corresponds, via a number of openings that are made along the respective conduit course in an inner wall of the supporting ring adjacent to the rotating body, with the gap between the rotating body and the supporting ring or with a corresponding line system inside the rotating body. Thus, the coolant from the first annular conduit flows through at least one of the aforementioned openings into the aforementioned gap or into a coolant supply line of the rotating body. The heated coolant is conducted, optionally via a coolant evacuation line of the rotating body, to the inner wall of the supporting ring and is evacuated, through at least a further one of the aforementioned openings, into the second annular conduit of the supporting ring. If the evacuation of the heated coolant is done from a coolant evacuation line of the rotating body, the openings in the supporting ring are distributed over the circumference of the supporting ring, expediently corresponding with the coolant evacuation line. A supply of coolant from the supporting ring to the rotating body and an evacuation of coolant from the rotating body into the supporting ring are attained regardless of the current rotary position of the rotating body.

For good separation between the supply and the evacuation of the coolant and for a structurally simple line layout, the first annular conduit discharges axially into the rotating body with respect to the supporting ring via the aforementioned openings, while the second annular conduit discharges radially into the rotating body with respect to the supporting ring. Conversely, the second annular conduit discharges axially into the rotating body with respect to the supporting ring, while the first annular conduit discharges radially into the rotating body.

The transverse and annular conduits described are especially suitable, for instance because of the large attainable conduit cross section, for achieving air cooling. Alternatively, however, a liquid can also be used as the coolant.

BRIEF DESCRIPTION OF THE DRAWINGS

Exemplary embodiments will be described in further detail below in conjunction with drawings. In the drawings.

Elements and sizes corresponding to one another are identified by the same reference numerals throughout the drawings.

DETAILED DESCRIPTION

Figure 1:
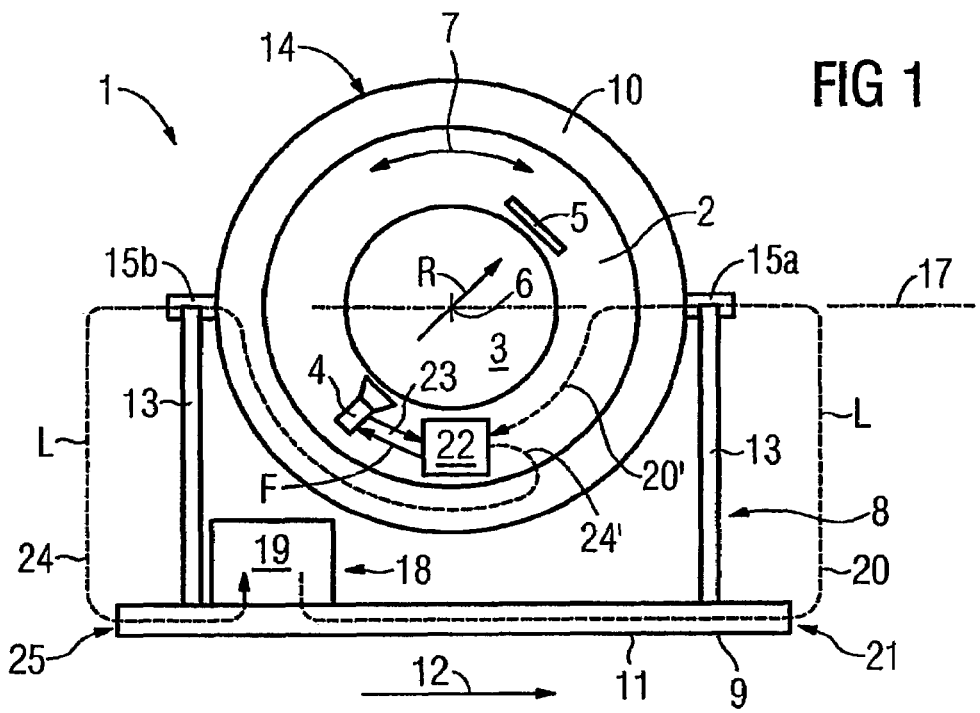
FIG. 1, in a schematic view, shows a support cradle, formed from a pedestal and a supporting ring, and a rotating body, rotatably supported on the supporting ring, as well as a cooling device for an X-ray emitter disposed in the rotating body.

FIG. 1 shows a computed tomography system 1 in a schematic sketch. The computed tomography system 1 includes a rotating body 2.

The rotating body 2 is penetrated by a central opening 3, into which an object to be examined (not further shown) can be positioned. In the usual medical application of a computed tomography system, the object to be examined is a patient to be examined.

The rotating body 2 includes an X-ray emitter 4 and, opposite the X-ray emitter 4, an X-ray detector 5. The X-ray emitter 4 is disposed such that X-radiation R can be passed through the object to be examined, located in the opening 3. An X-ray image made by the X-ray detector 5 is supplied, in operation of the computed tomography system 1, to an electronic evaluator (not shown), in particular a computer.

For generating a three-dimensional image of the object to be examined, the rotating body 2 is rotatable about an axis 6 that is perpendicular to the plane of FIG. 1 and is rotatable in the direction of the arrow 7. In this way, the object to be examined can be X-rayed from many directions. From the X-ray images made for different exposure directions, a three-dimensional image of the object being examined is generated in the electronic evaluator using mathematical methods.

The rotating body 2 is supported by a support cradle 8. The support cradle 8 includes a pedestal 9 and a gantry 10. The pedestal 9 includes a horizontal base plate 11 from which two struts 13, spaced apart in a transverse direction 12, protrude approximately at a right angle and hence vertically.

The gantry 10 (supporting element) is provided with two shaft segments 15a, 15b aligned with one another and each protruding from the outer circumference 14 of the gantry 10. Each shaft segment 15a, 15b is located in a corresponding guide 16 (FIGS. 2 and 3) on the associated strut 13. On the pedestal 9, the gantry 10 is rotatably supported about a horizontal transverse axis 17. The gantry 10 in turn rotatably supports the rotating body 2 about the common axis 6.

In operation of the computed tomography system, the X-ray emitter 4 in particular becomes quite hot. Further heat is generated to a lesser extent in the X-ray detector 5 as well. For dissipating this heat from the rotating body 2, the computed tomography system is equipped with a cooling device 18. The cooling device 18 includes a blower and cooling unit 19. The blower and cooling unit 19 blows cooled air L as coolant into a supply line 20 (indicated by a dashed-line arrow). The supply line 20 is initially guided, in a manner to be described in further detail below, by the base plate 11 of the pedestal 9. From one transverse end 21 of the base plate 11, the supply line extends via a hose connection or the like (not shown) and a hollow shaft segment 15a into the interior of the gantry 10. From there, the supplied air L is supplied to a supply line 20' of the rotating body 2. The supply line 20' discharges into a heat exchanger 22 disposed in the rotating body 2.

In the heat exchanger 22, the supplied air L is put into thermal contact with a primary cooling circuit 23, in the course of which the X-ray emitter 4 (and optionally the X-ray detector 5 as well) is disposed. The cooling circuit 23 includes a coolant liquid F, which flows around the outside or partly flows through the X-ray emitter 4. The coolant liquid F heated in the X-ray emitter 4 is cooled in the heat exchanger 22 by the cool air L. The air L heated in the process is returned to the blower and cooling unit 19 via an evacuation line 24 (represented by a dashed arrow).

From the heat exchanger 22, the heated air L is supplied in the course of the evacuation line 24 to the gantry 10 (the part of the evacuation line 24 associated with the rotating body 2 is designated here as 24'). Inside the gantry 10, the air L is supplied to the shaft segment 15b in a manner to be described in further detail below. From there, the air L is brought via a hose connection or the like (not shown in further detail here) to the transverse end 25 of the base plate 11 diametrically opposite the transverse end 21. Through the interior of the base plate 11, the air L is then again supplied to the blower and cooling unit 19.

The air loop formed by the supply line 20, 20' and the evacuation line 24, 24' is closed. The development of a draft, which is unwanted for health reasons, as a consequence of the recirculation of the air L is avoided.

Figure 2:
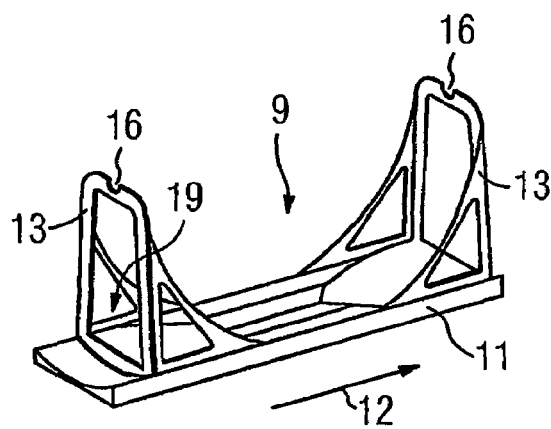
FIG. 2 shows the pedestal in perspective.
Figure 3:
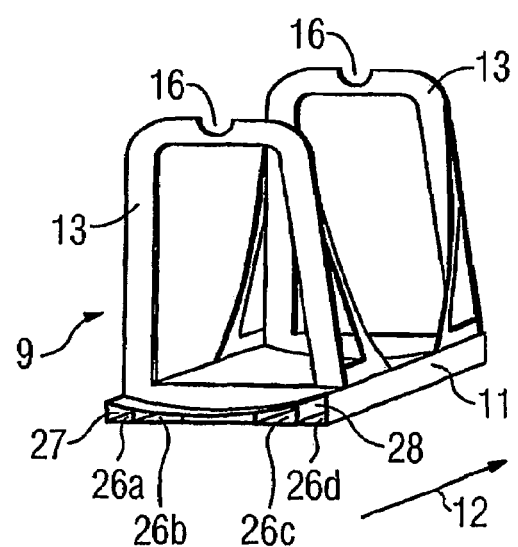
FIG. 3 shows the pedestal of FIG. 2, in a perspective view that is rotated relative to FIG. 2.

FIGS. 2 and 3 show the pedestal 9 of the computed tomography system 1 in perspective from different viewing angles. Particularly from FIG. 3, the base plate 11 is embodied as a hollow section, especially of sheet metal. In the interior of the base plate 11, a series of hollow chambers 26a through 26d is formed. The series extends in the longitudinal direction 12. The hollow chamber 26a is used here as a conduit 27 for evacuating the air L from the blower and cooling unit 19, and thus is used as part of the supply line 20. For this purpose, the hollow chamber 26a communicates with the outlet (not shown) of the blower and cooling unit 19. In the same way, the hollow chamber 26d is used as a transverse conduit 28 for returning the heated air L to the blower and cooling unit 19, and thus is used as part of the evacuation line 24. The transverse conduit 28 communicates for this purpose with the inlet (not shown) of the blower and cooling unit 19.

Figure 4:
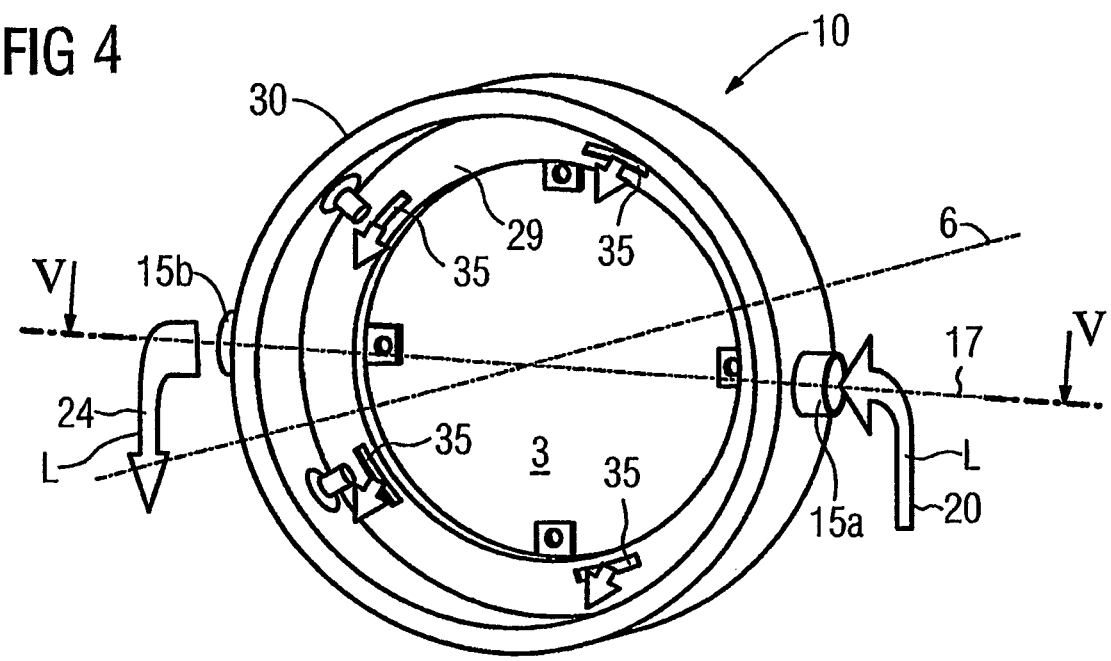
FIG. 4 shows the supporting ring of FIG. 1 in perspective.
Figure 5:
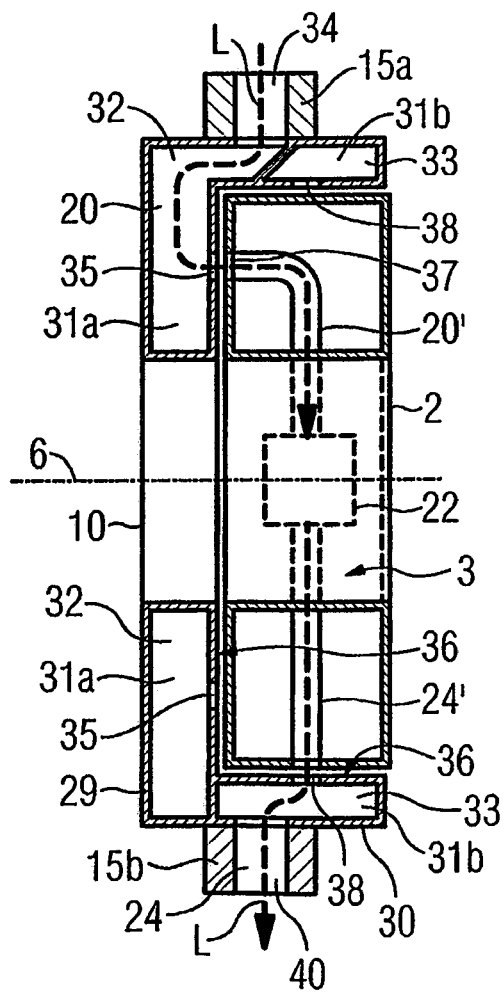
FIG. 5 is a schematic cross section V-V through the supporting ring of FIG. 4 along with a rotating body mounted in the supporting ring.

FIG. 4 shows the gantry 10 in perspective. A schematic cross section, which in particular is not to scale, along the line V-V through the gantry 10 and the rotating body 2 mounted in the gantry 10 is shown in FIG. 5. As can be seen from FIGS. 4 and 5, the gantry 10 is embodied as an annularly closed hollow section. The L-shaped section of the gantry 10 has a radial arm 29, from whose radially outer end an axial arm 30 extends approximately at a right angle. In each of the two arms 29 and 30, there is a respective hollow chamber 31a and 31b. The hollow chambers 31a, 31b are fluidically separated from one another and are used as annular conduits 32 and 33, respectively, for supplying and evacuating the air L. The annular conduit 32 disposed in the region of the radial arm 29 serves to supply the air L to the rotating body 2 and thus is a component of the supply line 20.

For supplying the air L, the annular conduit 32 communicates with a duct 34 through the hollow shaft segment 15a. Via a number of openings 35, which are made in the inner wall 36 of the gantry 10 facing toward the rotating body 2 in the region of the annular conduit 32, the annular conduit 32 corresponds with the supply line 20' of the rotating body 2. Thus, the annular conduit 32 discharges in the axial direction into the supply line 20' of the rotating body 2. The openings 35 are disposed in a circle around the axis 6. For every rotary position of the rotating body 2 relative to the gantry 10, at least one opening 35 overlaps an inlet 37 of the supply line 20'. In this way, the supply of air to the rotating body 2 is assured regardless of the rotary position of the rotating body.

The annular conduit 33 returns the air L from the rotating body 2 and is thus a component of the evacuation line 24. The return of the air L from the rotating body 2 into the annular conduit 33 is effected via a number of openings 38. The openings 38 are made in the axially oriented part of the inner wall 36 in the region of the annular conduit 33. The annular conduit 33 thus discharges in a radial direction into the evacuation line 24' of the rotating body 2. The openings 38 are distributed over the inside circumference of the gantry 10 at the same axial height of the supporting ring. For every rotary position of the rotating body 2 relative to the gantry 10, at least one opening 38 overlaps an outlet 39 of the evacuation line 24'. The evacuation of the air L from the rotating body 2 is also assured regardless of the rotary position of the rotating body 2. The annular conduit 33 opens, for evacuating the air L, toward a duct 40 of the hollow shaft segment 15b.

In an alternative, advantageously simplified embodiment, the rotating body 2 has no cooling device of its own in the form of a supply line for cold coolant and an evacuation line for heated coolant. Instead, the coolant is conducted through the gap between the rotating body 2 and the gantry 10. Cooling of the rotating body 2 takes place in this embodiment via the radial outer side of the rotating body 2, which for this purpose has good heat exchange properties or is equipped with heat exchanging devices.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

The invention claimed is:

1. A support cradle for a computed tomography system, the support cradle comprising:
   a rotating body;
   a supporting ring for rotatably supporting the rotating body, the supporting ring having a hollow section with first and second hollow chambers fluidically separated from one another, the first hollow chamber forming an annular conduit for supplying a coolant to the rotating body, and the second hollow chamber forming an annular conduit for evacuating the coolant from the rotating body.

2. The support cradle as defined by claim 1, wherein the support cradle includes a pedestal, on which the supporting ring is supported rotatably about a horizontal transverse axis.

3. The support cradle as defined by claim 2, wherein a base plate of the pedestal has a hollow section.

4. The support cradle as defined by claim 3, wherein two transverse conduits extend in the transverse direction and are fluidically separated from one another in the base plate.

5. The support cradle as defined by claim 1 wherein the supporting ring has a substantially L-shaped profile, and wherein one of the annular conduits is in a first arm of the L-shaped profile, and the other of the annular conduits is in a second arm of the L-shaped profile.

6. The support cradle as defined by claim 1 wherein the supporting ring is supported with two aligned shaft segments secured to a circumference of the supporting ring, by a pedestal, and at least one shaft segment is a hollow section and communicates, for supplying or evacuating the coolant, with a corresponding annular conduit of the supporting ring.

7. The support cradle as defined by claim 1 wherein, along the course of each annular conduit, a number of openings are made in an inner wall of the supporting ring.

8. The support cradle as defined by claim 7, wherein a first annular conduit discharges axially with respect to the supporting ring onto an adjacent outer side of the rotating body, and wherein a second annular conduit discharges radially with respect to the supporting ring onto a wall of the rotating body.

9. The support cradle as defined by wherein the coolant is air.

10. The support cradle as defined by claim 4 wherein the supporting ring has a substantially L-shaped profile, and wherein one of the annular conduits is in a first arm of the L-shaped profile, and the other of the annular conduits is in a second arm of the L-shaped profile.

11. The support cradle as defined by claim 2 wherein the supporting ring is supported with two aligned shaft segments secured to a circumference of the supporting ring by the pedestal, and at least one shaft segment is a hollow section and communicates, for supplying or evacuating the coolant, with a corresponding annular conduit of the supporting ring.

12. A computed tomography system comprising:
    a blower and cooling unit;
    a supply line;
    an evacuation line for a cooling device that includes coolant; and
    a support cradle at least partly receiving the supply line and evacuation line and rotatably supporting a rotating body the support cradle having a hollow section with first and second hollow chambers fluidically separated from one another, the first hollow chamber forming an annular conduit for supplying the coolant to the rotating body, and the second hollow chamber forming an annular conduit for evacuating the coolant from the rotating body.

13. The computed tomography system as defined by claim 12, wherein the blower and cooling unit is disposed on a base plate and, for recirculating and cooling the coolant, is in fluidic communication with transverse conduits of the base plate.

14. The computed tomography system as defined by claim 12, wherein the first hollow chamber of the support cradle corresponds via first openings with a supply line of the rotating body; and wherein the second hollow chamber of the support cradle corresponds via second openings with an evacuation line of the rotating body.

* * * * *

UNITED STATES PATENT AND TRADEMARK OFFICE
CERTIFICATE OF CORRECTION

PATENT NO. : 7,393,138 B2 Page 1 of 1
APPLICATION NO. : 10/580150
DATED : July 1, 2008
INVENTOR(S) : Edgar Schindler et al.

It is certified that error appears in the above-identified patent and that said Letters Patent is hereby corrected as shown below:

On the Title Page

Item (57), line 1, under "ABSTRACT", after "a computer", delete "tomorgraph" and substitute --tomograph-- in its place.

Item (57), lines 3-4, under "ABSTRACT", after "emitter, can be" delete "ratably" and substitute --rotatably-- in its place.

In column 6, in claim 9, line 1, after "as defined by" insert --claim 1--.

Signed and Sealed this

Seventeenth Day of March, 2009

JOHN DOLL
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 7,393,138 B2 | Page 1 of 1 |
| APPLICATION NO. | : 10/580150 | |
| DATED | : July 1, 2008 | |
| INVENTOR(S) | : Edgar Schindler et al. | |

It is certified that error appears in the above-identified patent and that said Letters Patent is hereby corrected as shown below:

On the Title Page

Item (57), line 1, under "ABSTRACT", after "a computer", delete "tomorgraph" and substitute --tomograph-- in its place.

Item (57), lines 3-4, under "ABSTRACT", after "emitter, can be" delete "ratably" and substitute --rotatably-- in its place.

In column 6, in claim 9, line 29, after "as defined by" insert --claim 1--.

This certificate supersedes the Certificate of Correction issued March 17, 2009.

Signed and Sealed this

Seventh Day of April, 2009

JOHN DOLL
*Acting Director of the United States Patent and Trademark Office*